United States Patent
Terrisse

(10) Patent No.: US 9,907,881 B2
(45) Date of Patent: Mar. 6, 2018

(54) CROSSLINKED, HYDROPHOBIC ACRYLIC COPOLYMER MADE OF 2-PHENOXYTETRAETHYLENE-GLYCOL ACRYLATE AND INTENDED FOR INTRAOCULAR LENSES

(71) Applicant: ACRYLIAN, Strasbourg (FR)

(72) Inventor: Jean Terrisse, Strasbourg (FR)

(73) Assignee: ACRYLIAN, Strasbourg (FR)

( * ) Notice: Subject to any disclaimer, the term of this patent is extended or adjusted under 35 U.S.C. 154(b) by 127 days.

(21) Appl. No.: 15/110,350

(22) PCT Filed: Jan. 26, 2015

(86) PCT No.: PCT/FR2015/050172
§ 371 (c)(1),
(2) Date: Jul. 7, 2016

(87) PCT Pub. No.: WO2015/128555
PCT Pub. Date: Mar. 9, 2015

(65) Prior Publication Data
US 2016/0331864 A1    Nov. 17, 2016

(30) Foreign Application Priority Data

Feb. 27, 2014  (FR) ...................... 1451578

(51) Int. Cl.
| | |
|---|---|
| *C08F 220/30* | (2006.01) |
| *A61F 2/16* | (2006.01) |
| *A61L 27/16* | (2006.01) |
| *A61L 27/50* | (2006.01) |
| *C08F 220/68* | (2006.01) |
| *C08J 3/24* | (2006.01) |

(52) U.S. Cl.
CPC ............... *A61L 27/16* (2013.01); *A61F 2/16* (2013.01); *A61L 27/50* (2013.01); *C08F 220/68* (2013.01); *C08J 3/24* (2013.01); *A61F 2002/169* (2015.04); *A61F 2002/1696* (2015.04); *A61L 2430/16* (2013.01); *C08F 220/30* (2013.01); *C08F 2220/302* (2013.01); *C08F 2220/306* (2013.01)

(58) Field of Classification Search
CPC .. C08F 220/30; C08F 220/68; C08F 212/145; C08F 2220/302; C08F 2220/306; A61L 27/16; A61L 27/50; A61L 2430/16; A61F 2/16; A61F 2002/169; A61F 2002/1696; C08J 3/24
See application file for complete search history.

(56) References Cited

U.S. PATENT DOCUMENTS

| | | | |
|---|---|---|---|
| 4,904,421 | A | 2/1990 | Ando et al. |
| 6,326,448 | B1 | 12/2001 | Ojio et al. |
| 6,465,588 | B1 | 10/2002 | Li |
| 6,713,584 | B1 | 3/2004 | Chisholm et al. |
| 8,470,034 | B2 | 6/2013 | Terrisse |
| 2009/0088493 | A1 | 4/2009 | Water et al. |
| 2011/0245442 | A1* | 10/2011 | Terrisse ............... A61F 2/1613 526/227 |

FOREIGN PATENT DOCUMENTS

| | | |
|---|---|---|
| FR | 2930731 A1 | 11/2009 |
| WO | 2001005578 A1 | 1/2001 |
| WO | 2001018079 A1 | 3/2001 |

OTHER PUBLICATIONS

International Search Report issued in PCT/FR2015/050172, dated Jul. 30, 2015.

* cited by examiner

*Primary Examiner* — Roberto Rabago
(74) *Attorney, Agent, or Firm* — Heslin Rothenberg Farley & Mesiti P.C.

(57) ABSTRACT

The material according to the invention is a hydrophobic, cross-linked, acrylic copolymer of at least the following monomers:
  an arylalkoxy-acrylate different from a 2-phenoxy-(2-ethoxy)$_n$-acrylate with 4≤n≤6;
  a 2-phenoxy-(2-ethoxy)$_n$-acrylate with 4≤n≤6, preferably 2-phenoxy-tetraethylene-glycol acrylate;
  a hydroxylated acrylate;
  a hydroxylated methacrylate;
  an ethoxylated diol diacrylate; and
  an ethoxylated diol dimethacrylate.
It is obtained in one single step of radical polymerization, in the presence of a transfer agent during the cross-linking. It thus has a physical structure corresponding to a three-dimensional macromolecular network with hanging chains. This material is used for manufacturing intraocular lenses (1) with low glistening that are not self-adhering.

20 Claims, 1 Drawing Sheet

CROSSLINKED, HYDROPHOBIC ACRYLIC COPOLYMER MADE OF 2-PHENOXYTETRAETHYLENE-GLYCOL ACRYLATE AND INTENDED FOR INTRAOCULAR LENSES

CROSS REFERENCE TO RELATED APPLICATIONS

This application is a national stage filing under section 371 of International Application No. PCT/FR2015/050172, filed on Jan. 26, 2015, and published on Sep. 3, 2015 as WO/2015/128555, and claims priority to French Application No. 1451578, filed on Feb. 27, 2014. The entire disclosures of each of the prior applications are hereby incorporated herein by reference.

The invention herein concerns a new hydrophobic, acrylic polymer material perfectly suitable for the manufacturing of intraocular lens.

The invention also concerns intraocular lens made from such a polymer material.

Intraocular lenses are opthalmologic implants or prostheses that are placed surgically in the eye of patients suffering, for example, from cataracts, as a replacement for their defective crystalline lens.

During the operation, the surgeon makes a small incision in the patient's cornea, through which he removes the patient's dysfunctional natural crystalline lens. He then places the intraocular lens in position in the crystallin bag instead of the removed crystalline lens, through this incision.

The lens conventionally incorporates a corrective optical part, of which the correction varies from 10 to 30 diopters, depending on the case. This optical part is essentially disc-shaped and has a generally asymmetrical biconvex cross-section. It must be positioned perpendicularly, centered in relation to the optical axis of the eye.

From this central optical part extends lateral extensions called haptics, the role of which is to place tension upon the walls of the crystalline bag and ensure proper positioning of the lens in relation to them.

To make the operation as least traumatizing as possible for the patient, and to prevent the development of a post-operational astigmatism, the incision made in the cornea must be as small as possible.

During the operation to place the intraocular lens, the lens is rolled up in an injector the exit end of which is inserted into the crystalline bag through the incision.
The intraocular lens, which has a diameter that is considerably bigger than the length of the incision, has to be extremely compressed to be able to be ejected through the exit end of the injector, the outside diameter of which is smaller than that of the incision.

Once it has been released into the crystalline bag, the intraocular lens must deploy itself quickly in order to position itself properly and be capable of fulfilling its function of optical correction in a satisfactory manner.

Because of their nature intending them to be permanently implanted within a human eye, the optical function that they have to fulfill and their very difficult implantation process, intraocular lenses are subjected to very many constraints and must fulfill multiple criteria simultaneously in order to be satisfactory.

From an optical viewpoint, the intraocular lens must be made of a transparent material of suitable optical index, namely greater than 1.5 and must be able to focus on the macula once the lens is in position, while being of small size.

The material must allow high-precision machining to obtain the necessary optical quality.

Moreover, the lens must not cause any problem of dazzling, and must not whiten and become diffusive over time or during temperature changes within the range of temperatures that can normally be encountered.

The material used for their production must be compatible with permanent implantation within the human eye, and must not be cytotoxic. Over time, it must not disseminate any toxic substances, so as not to cause necroses.

Furthermore, for the lens to be fitted without problem, the material must be sufficiently flexible to be folded and rolled up. It must withstand considerable elongation and the thrusting pressure without breaking itself or breaking the injection tube, so as to pass through a very small ejection aperture of around 1.5 mm diameter or even less.

Lastly, once in the patient's eye, the intraocular lens must be capable of deploying itself alone and within a few seconds, without sticking to itself, so as to position itself correctly in the crystalline bag and recover its optical characteristics.

Many intraocular lenses of various shapes and compositions have been proposed in prior art. However, despite the very wide variety proposed, until present, none has managed to fulfill all of these criteria in a satisfactory manner.

The purpose of the invention is to provide a new material allowing the production of intraocular lenses that fulfill all of these conditions.

In prior art, it has been attempted to develop more flexible materials, to make intraocular lenses that are easier to insert through an ever-smaller incision.

Although more flexible, lenses made of so-called "hydrophilic" plastic materials pose problems of inflammation of the eye, because of the dissemination of substances escaping from these lenses, which are difficult to purify and which always stay in equilibrium with the water of the eye in which they are implanted.

Furthermore, hydrophilic materials such as the hydrogels conventionally used for making intraocular lenses accelerate the migration of epithelial cells on the surface of the lenses and, in the long-term, can be responsible for a capsular opacification that is a particular nuisance for the patient.

Instead, so-called "hydrophobic" plastic materials have been adopted that are defined by a water absorption of less than 5% at 35° C., and that have specific characteristics that do not depend on the quantity of water absorbed. During production, they can be easily purified, and extractable substances that are insoluble in water can be removed.

Such is the case, for example, of acrylic polymers or silicon-based polymers.

The flexibility of these materials depends on their temperature. They have a vitreous transition temperature (Tg) below which they are hard and can be machined, and above which they become flexible, distortable and elastic.

For the manufacturing of intraocular lenses, one must choose a material having a vitreous transition temperature that is sufficiently low for the resulting lens to be enough flexible to rolled and stretched at surgical room temperature, namely 18 to 20° C.

The invention falls within the scope of these so-called "hydrophobic" plastic materials, and more-specifically concerns acrylic polymers.

The well-known problem of these hydrophobic materials is that the more flexible and distortable they are, the stickier they are.

Accordingly, the intraocular lenses can have difficulty in deploying properly when they are implanted in the patient's eye. In particular, the haptics very often remain bonded to the optical part of the lens.

To resolve this technical problem, an acrylic polymer designed for the production of intraocular lenses has been proposed in prior patent application FR 2 930 731.

This material is obtained by radical polymerization from a mixture that contains the following monomers:
  an arylalkoxy-acrylate or an arylalkoxy-methacrylate;
  an alkylacrylate, preferably butyl acrylate;
  a hydroxylated acrylate;
  a hydroxylated methacrylate;
  a diol diacrylate; and
  a diol dimethacrylate.

The deformability of the resulting polymer has been considerably improved by the addition of a transfer agent, such as thiol butane or thiol octane, to the initial mixture of monomers.

But even though this polymer material has undeniable qualities in relation to the other materials commercially-available, it has two major disadvantages that prevent it from resolving the technical problem in a satisfactory manner.

Firstly, the material remains tacky on the surface, which prevents the rapid deployment of the intraocular lens once it has been released in the crystalline bag.

With such a polymer material, it still happens that the haptics remain bonded to the optical part of the lens, obliging the surgeon to attempt to unbond them manually through the incision in the cornea. This hazardous operation is particularly delicate.

Furthermore, lenses produced with this polymer material have a certain susceptibility to whitening in tepid water also called "glistening" which proves problematic.

The "glistening" phenomenon is an undesirable effect that frequently and principally affects hydrophobic acrylic lenses by modifying the transparency of their optics. When these lenses are immersed in an aqueous medium, such as is the case when they are implanted in the eye of a patient, they form micro-vacuoles of water within the polymer material that are visible because of the difference in optical index existing between the water and the polymer.

As the quantity of water that is absorbed by the material varies according to the temperature, the formation of vacuoles is influenced by temperature variations. When the temperature varies quickly for instance, when the patient enters a heated indoor location from outdoors during the winter, or enters an air-conditioned location from warm outdoor temperatures during the summer, or vice versa vacuoles of water appear or disappear, which locally modifies the transparency of the intraocular lens and causes a localized glistening. One observes the appearance of local turbidities, sparkles or whitish "clouds" in the field of view, which can cause a nuisance or a reduction of the visual acuity.

The invention offers a different solution to this problem by providing a new material for the production of intraocular lenses, that is non-tacky by nature, and that has a very low susceptibility to glistening that, in particular, is considerably lower than that of the prior material discussed above.

Surprisingly, this new material resolves both the problem of glistening and that of the unbonding of the haptics and quick deployment of the lens once it has been implanted in the eye, while conserving the characteristics essential for the targeted application and the advantages of the aforesaid prior material.

To resolve this technical problem, the invention provides a new hydrophobic, acrylic polymer material intended for the production of intraocular lenses.

This material is a cross-linked copolymer of at least the following monomers:
  an arylalkoxy-acrylate different from a 2-phenoxy-(2-ethoxy)$_n$-acrylate with $4 \leq n \leq 6$;
  a 2-phenoxy-(2-ethoxy)$_n$-acrylate with $4 \leq n \leq 6$, preferably 2-phenoxy-2-ethoxy-2-ethoxy-2-ethoxy-2-ethoxy-acrylate;
  a hydroxylated acrylate;
  a hydroxylated methacrylate;
  an ethoxylated diol diacrylate; and
  an ethoxylated diol dimethacrylate.

This cross-linked copolymer takes the form of a three-dimensional macromolecular network with hanging chains, due to the presence of at least one transfer agent in the monomer mixture during the cross-linking.

The polymer no longer contains alkylacrylate monomers and, in particular, butyl acrylate, because the present inventors have observed that it was particularly responsible for the tacky nature of the surfaces.

On the other hand, it contains 2-phenoxy-(2-ethoxy)$_n$-acrylate (with $4 \leq n \leq 6$) as monomer. Thanks to its ethoxy functions, which are uniformly distributed in the resulting polymer, this co-monomer slightly increases the amphiphilic character of the material. The solubility of the water in the material is slightly increased but remains controlled.

The presence of ethoxylated sub-chains, however, enables the excess concentrations of water that can occur during small temperature variations to be broken down into numerous sub-domains of small size at the scale of the macromolecular network. These small sub-domains are distributed uniformly, and are attached to the network. Therefore, they cannot group in order to absorb a greater quantity of water.

They no longer form vacuoles of water of sufficient size to be visible in natural light and thus be responsible for the glistening phenomenon. They are replaced by clusters of water that are more-numerous but are much smaller (of nanometric size) located within short polyethoxylated sub-chains that, because of their very small size, are not diffusive of natural light.

Furthermore, these clusters are located in sub-domains of lower index (approximately 1.48) than that of the surrounding material (around 1.54). The contrast with the index of the water (1.33) is lower, which makes these clusters less visible.

For all these reasons, the material's susceptibility to glistening (whitening) is much smaller.

This monomer also considerably reduces the tacky nature of the surfaces on themselves, such as will be demonstrated further on.

The invention also teaches a method for the production of the acrylic polymer material according to the invention, in which:
  a mixture containing at least one arylalkoxy-acrylate different from a 2-phenoxy-(2-ethoxy)$_n$-acrylate with $4 \leq n \leq 6$, one 2-phenoxy-(2-ethoxy)$_n$-acrylate with $4 \leq n \leq 6$, one hydroxylated acrylate, one hydroxylated methacrylate, one ethoxylated diol diacrylate, one ethoxylated diol dimethacrylate, and one transfer agent, is realized;
  this mixture is radically polymerized, in one single polymerization step, such that to obtain by this polymerization a three-dimensional macromolecular network with hanging chains.

After radical polymerization, the polymer is free of residual fractions of monomers and other additives not having been polymerized.

After this purification stage, a material that has the physical properties stated in this application herein is obtained.

Lastly, the invention provides intraocular lenses to be surgically implanted in the crystalline bag of a patient, as a replacement for his/her natural crystalline lens, produced from the acrylic polymer material according to the invention.

Such intraocular lenses are particularly advantageous because the polymer material according to the invention fulfills all the criteria necessary for overcoming the numerous constraints in the targeted application.

Indeed, it has a optical index that is high—greater than 1.5—but that is insufficient to cause the multiple reflection phenomena causing the dazzling problem. This index is preferably between 1.53 and 1.56, with a preferred value of 1.545.

The material has a low vitreous transition temperature that allows it to be particularly flexible, distortable and elastic at the temperature of implantation of the lens and at the temperature of the eye. Its vitreous transition temperature is advantageously 5° C. or lower and, for example, around 2 to 3° C.

Despite this low vitreous transition temperature, it remains easily machinable by chip removal at machining temperatures of −15 to −20° C. The variation in physical properties is actually very sudden as from −5° C.

It has a great aptitude for distortion without breaking at the usage temperatures, namely between 18 and 35° C. With a modulus of elasticity lower than 0.4 MPa at 30° C. and an elongation at break of 250% or greater under compression, it can easily be rolled and strongly stretched in the injection cartridge to be implanted in the patient's eye.

Thanks to its high surface tension due to the presence of hydroxylated monomers, the material according to the invention does not adhere to itself either in the dry state or the wet state. Therefore, it can deploy easily and entirely once in position in the patient's eye, and thus satisfactorily resolves the problem of haptics remaining bonded to the optical part of intraocular lenses.

This deployment is achieved quickly due to the short time of relaxation of the material according to the invention, which is less than 15 seconds at a temperature of 20° C. and less than 5 seconds at 30° C.

The purified material has a water absorption rate lower than 4% at a temperature of 40° C. and lower than 3.5% at 30° C.

Other characteristics and advantages of the invention will become apparent on reading the detailed description that follows, particularly the role, preferred nature and quantity of each of the monomers and other constituent parts of the mixture allowing to obtain the material according to the invention.

To facilitate the reader's proper understanding, this description is accompanied by the following appended drawings, by way of example:

Figure 1:
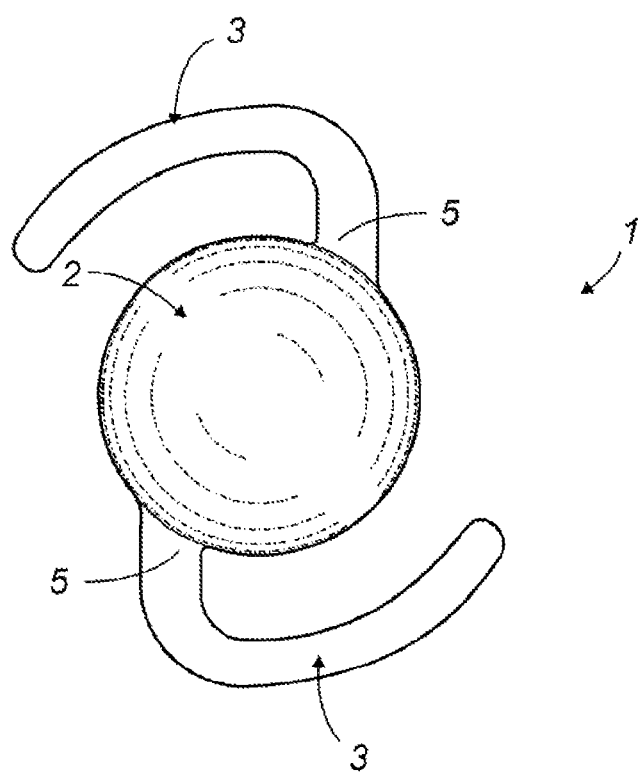
FIG. 1 is a first example of an intraocular lens that can be made using the material according to the invention.
Figure 2:
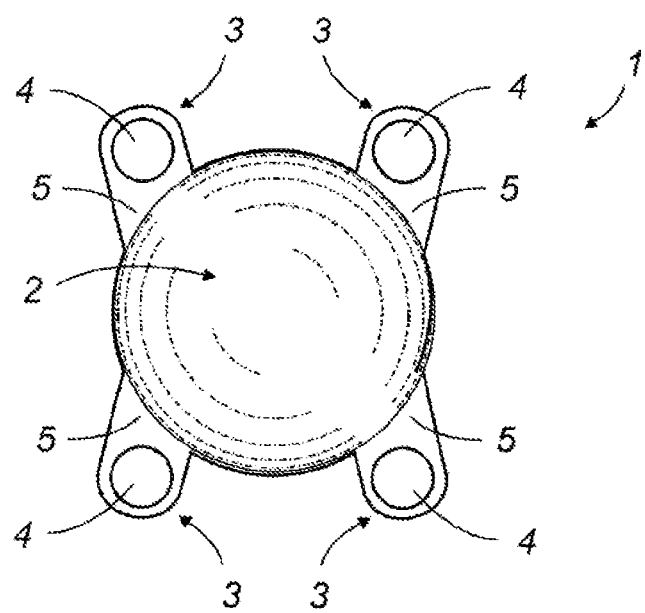
FIG. 2 is a second example of an intraocular lens that can be made using the material according to the invention.

In FIGS. 1 and 2, two conventional examples of an intraocular lens 1 has been illustrated that can be produced using the acrylic polymer material according to the invention.

These lenses 1 comprise a central optical part 2 that is essentially disc-shaped and has a bi-convex profile.

Extending from this optical part 2, there are lateral extensions called haptics 3.

In FIG. 1, there are two of these haptics 3. They are located in diametrically-opposed positions and have the shape of a curved arm, with each extending in an opposing direction.

The lens in FIG. 2 has four haptics 3 that are shaped like a pierced ring with a central opening 4. These haptics 3 are regularly distributed around the periphery of the optical part 2.

In the examples illustrated, the haptics 3 are manufactured as one piece with the optical part 2 of the lens 1. This type of lens is called a "one-piece lens". The material according to the invention is particularly suitable for the production of such lenses.

The haptics 3 are joined to the central optical part 2 via a connecting area 5 forming a hinge that generates a spring effect through elastic return of the material to unfold the lens during its implantation into the eye of a patient.

The material according to the invention is particularly suitable for the production of such lenses 1.

It is a cross-linked, hydrophobic, acrylic co-polymer of at least the following monomers:
an arylalkoxy-acrylate different from a 2-phenoxy-(2-ethoxy)$_n$-acrylate with 4≤n≤6;
a 2-phenoxy-(2-ethoxy)$_n$-acrylate with 4≤n≤6;
a hydroxylated acrylate;
a hydroxylated methacrylate;
an ethoxylated diol diacrylate; and
an ethoxylated diol dimethacrylate.

Its physical structure is a three-dimensional macromolecular network that locally incorporates hanging chains. This is due to the action, during the reticulation, of a transfer agent added to the mixture of monomers before polymerization.

The use of an arylalkoxy-acrylate, which has a relatively-low vitreous transition temperature, enables to obtain a final polymer with a high optical index.

As arylalkoxy-acrylate different from a 2-phenoxy-(2-ethoxy)$_n$-acrylate with 4≤n≤6, a compound chosen from 2-phenoxy-ethylacrylate, 2-phenoxy-2-ethoxy-ethylacrylate or 2-phenoxy-2-ethoxy-2-ethoxy-ethylacrylate can be used.

As a preferred example, 2-phenoxy-ethylacrylate can be cited.

The initial mixture before polymerization preferably comprises between 45 and 84% by weight of arylalkoxy-acrylate different from a 2-phenoxy-(2-ethoxy)$_n$-acrylate with 4≤n≤6. Preferably, it contains between 70 and 80% by weight of it.

A monomer with ethoxylated sub-chain of type 2-phenoxy-(2-ethoxy)$_n$-acrylate, with n equal to 4, 5 or 6, is added to the mixture.

The monomer with ethoxylated sub-chain used can advantageously be 2-phenoxy-2-ethoxy-2-ethoxy-2-ethoxy-2-ethoxy-acrylate (n=4), also called 2-phenoxy-2-tetraethylene glycol acrylate, or acrylate of 2-phenoxy-2-tetraethylene glycol acrylate, or acrylic monoester of phenylether of tetraethylene glycol, or else 4PEA.

The initial mixture before polymerization preferably includes between 3 and 15% by weight of 2-phenoxy-(2-ethoxy)$_n$-acrylate, more preferably between 4 and 10%, and preferably around 6%.

This monomer enables to lower the vitreous transition temperature of the resulting polymer while endowing it with as certain hydrophily.

As will be demonstrated further on, it also advantageously enables to lower the self-adhering tendency of the surfaces, and to very strongly reduce the glistening of the obtained polymer material.

To decrease the tacky nature of the material in the humid state, the final polymer must have a sufficient quantity of hydroxyl functions on the surface. The water thus forms a continuous film on the surface of the material that prevents the material from adhering to itself.

Hydroxylated monomers: a hydroxylated acrylate and a hydroxylated methacrylate are thus added to the mixture, and increase the surface tension and the water affinity of the surface of the resulting polymer.

These polymers thus contribute to preventing the material and, therefore, the lens made from it, from whitening on prolonged contact with water at 35° C., by migration of species not linked to the polymer network and having a strong affinity with water.

To be compatible with the specification, when in the polymerized and dry state, these monomers must not have an excessively-high vitreous transition temperature, namely higher than 10° C.

The hydroxylated acrylate used is, for example, a dihydroxy-alkyl mono-acrylate or a dihydroxy-ethoxy-alkyl mono-acrylate of which the alkyl chain of the glycol incorporates 3 to 6 atoms of carbon. One can cite, for example, 4-hydroxy-butyl acrylate, also known as acrylate of 4-hydroxy-butyl or butanediol acrylate, hexanediol acrylate or triethylene glycol mono-acrylate.

The hydroxylated methacrylate used is, for example, a dihydroxy-alkyl mono-methacrylate or a dihydroxy-ethoxy-alkyl mono-methacrylate of which the alkyl chain of the glycol incorporates 3 to 6 atoms of carbon. It can be, for example, hydroxy-ethyl methacrylate, butanediol monomethacrylate, hexanediol monomethacrylate or triethylene glycol mono-methacrylate; glycols with a chain of more than 3 carbon atoms are preferred because they have a vitreous transition temperature lower than that of hydroxyethyl methacrylate.

The proportion of these hydroxylated monomers in the mixture before polymerization must not however be too big for the resulting material to remain globally hydrophobic and not to absorb more than 5% of water at 35° C.

Advantageously, the hydroxylated acrylate and the hydroxylated methacrylate together represent preferably between 10 and 20% by weight of the mixture, and more preferably, around 11 to 15% of the mixture.

Depending on the case, the proportion of these two hydroxylated monomers relative to one another may vary from 20 to 80% for one of them and conversely for the other, as a function of the desired vitreous transition temperature.

The mixture also contains cross-linking compounds allowing to obtain, during the polymerization, a three-dimensional macromolecular network and not linear polymers. To obtain such a mesh, difunctional monomers are added: an ethoxylated diol diacrylate and an ethoxylated diol dimethacrylate.

These cross-linking compounds comprise ethoxy functions so as not to augment the vitreous transition temperature of the final material and, in parallel, to maintain a hydrophily level that is homogeneous with the rest of the composition.

The used ethoxylated diol diacrylate is preferably triethylene glycol diacrylate or tetraethylene glycol diacrylate.

The used ethoxylated diol dimethacrylate can be triethylene glycol dimethacrylate or tetraethylene glycol dimethacrylate.

The quantity of cross-linking agents must be sufficient to avoid too many long hanging chains rich in arylalkoxy-acrylate in the final polymer, since they increase the tacky nature of the polymer.

Furthermore, the higher the cross-linking rate, the shorter the polymer relaxation time is; the lens deploying itself more quickly in the eye at constant vitreous transition temperature.

However, the resulting polymer becomes brittle when its cross-linking rate is too high.

The quantity of ethoxylated diol diacrylate and ethoxylated diol dimethacrylate must therefore be chosen carefully. Preferably, these cross-linking compounds are added to the mixture in quantities such that the final cross-linking level is a mass between cross-linking nodes comprised between 2000 g/M and 10000 g/M.

Advantageously, the ethoxylated diol diacrylate and ethoxylated diol dimethacrylate together preferably represent between 1 and 3% by weight of the mixture, with the relative proportion between the ethoxylated diol diacrylate and the ethoxylated diol dimethacrylate preferably varying between 20 to 80% of one in relation to the other, and vice versa.

By summarizing the considerations discussed above, it is possible to imagine a particular mixture of monomers giving rise, by radical polymerization, to a preferred embodiment of the material according to the invention.

This mixture preferably includes at least the following monomers: 2-phenoxy-ethylacrylate; 2-phenoxy-2-ethoxy-2-ethoxy-2-ethoxy-2-ethoxy-acrylate; 4-hydroxy-butyl-acrylate; hydroxy-ethyl methacrylate; tetraethylene glycol diacrylate; and tetraethylene glycol dimethacrylate.

However, the material according to the invention is not limited to the aforementioned monomers; other monomers can obviously be added to the mixture, such as—for example—triethylene glycol dimethacrylate, which can be added in addition to the tetraethylene glycol diacrylate and the tetraethylene glycol dimethacrylate, so as to adjust the cross-linking level.

It is also possible to add to the monomers one or more polymerizable or non-polymerizable colorants, or one or more anti-UV agents, the function of which in the final material is to absorb ultraviolet rays. It can be, for example, 2-[3-(2H-benzotriazol-2-yl)-4-hydroxyphenyl]ethyl-methacrylate, which is preferably used with a proportion between 0.1% and 1% by weight, and, for example, a content of 0.5%.

Any other monomer or any other polymerizable or non-polymerizable constituent imaginable by a man skilled in the art, with whatever function, can be added to the mixture without falling outside the scope of the invention herein, as long as its presence does not modify the general properties of the resulting polymer material such as to make it unsuitable for the production of intraocular lenses.

The acrylic polymer material according to the invention is obtained by a radical polymerization method that includes one single polymerization step, with the polymerization and the cross-linking taking place simultaneously during the same step of the process.

For this, one starts by producing a mixture of all the monomers necessary for the production of the polymer material according to the invention.

This mixture contains at least one arylalkoxy-acrylate different from a 2-phenoxy-(2-ethoxy)$_n$-acrylate with $4 \leq n \leq 6$, one 2-phenoxy-(2-ethoxy)n-acrylate with $4 \leq n \leq 6$, one hydroxylated acrylate, one hydroxylated methacrylate, one ethoxylated diol diacrylate, and one ethoxylated diol dimethacrylate.

It also contains at least one transfer agent. It may be a halogenated product or, more preferably, a compound from the thiol family, such as—for example—thiol butane or thiol octane.

A transfer agent is defined as being a chemical compound that, during the radical polymerization, captures a radical on a macromer and transfers it to a new monomer to propagate the reaction.

Transfer agents are chemical compounds well known to a man skilled in the art. There is, for instance, a definition and a comprehensive list in the following reference work: "Polymer Handbook, Fourth Edition, Volume 1, Editors: J. Brandrup, E. H. Immergut, and E. A. Grulke" in the article entitled "Transfer constants to monomers, polymers, catalysts and initiators, solvents and additives, and sulfur compounds in free radical polymerization" by A. Ueda and S. Nagai, in Part II, page 97 and after.

Strongly cross-linked acrylic polymers are known for being fragile and brittle, which gives rise to an elongation at break that is inversely proportional to the cross-linking rate.

The addition of a small quantity of transfer agent to the initial monomer mixture before polymerization and therefore cross-linking, enables to reduce this property, which is particularly undesirable for the targeted application, because intraocular lenses undergo extreme distortion and extension during their implantation within the eye of the patient.

The transfer agent advantageously augments the aptitude for distortion without breakage of the resulting polymer material. The addition to the mixture of a transfer agent enables to obtain a high cross-linking rate while conserving an important elongation at break.

This transfer agent locally stops the polymerization by transferring the radical of a cross-linked macromer to a monomer. The formation of the three-dimensional meshwork is thus locally interrupted and one obtains, at this level, a cut mesh with a short hanging chain linked to the network but with the other end unattached. Therefore, the transfer agent provides a later meshwork capable of stretching more without breaking.

At the end of polymerization in the presence of the transfer agent, the cross-linked co-polymer obtained is a three-dimensional macromolecular network with hanging chains.

Advantageously, a very small quantity of transfer agent is necessary to obtain this result. The initial mixture thus contains preferably between 0.03% and 0.2% by weight of transfer agent, and yet more preferably between 0.04% and 0.15% of transfer agent, 0.05% being a preferred value for thiol butane and 0.1% for thiol octane.

In addition to monomers, the initial mixture can contain a certain number of additional compounds of different nature necessary, for example, for the satisfactory progress of the reaction.

It includes, for instance, one or more initiator compounds that prime the polymerization reaction by creating active sites on the monomers. It/they thus enable one to adjust the kinetics of the polymerization reaction.

This or these initiator compound(s) can, for example, be chosen from among alkyl peroxides, lauroyl diperoxide (commonly called lauroyl peroxide), 1,1-di-ter-butylperoxy-cyclohexane or tert-amyl-peroxy-2-ethyl-hexyl-carbonate, also known as Taec.

This or these compound(s) are added to the mixture in very small quantities; the mixture includes, for instance, between 0.3 and 2% by weight of initiator compound.

To make this description more comprehensive, we will now describe an example of a method for obtaining the acrylic polymer material according to the invention, from the initial mixture explained above.

To produce the sought-after polymerization, one starts by mixing together all the different monomers necessary for the reaction. Advantageously, these monomers are soluble in each other, and simple stirring is sufficient for achieving a homogeneous mixture of them.

The initiator compound or compounds are then added to this mixture such as necessary for triggering the polymerization reaction.

The transfer agent is also added to the mixture before or after the initiator compound.

Then, the polymerization is realized radically in one single step.

For this, small quantities of this mixture are placed in molds and heated to a temperature between, for example, 75° C. and 95° C.

Once the reaction is finished and after cooling, the polymer is released from the mold.

The molds are preferably chosen so as to obtain, after mold release, polymer blocks of general cylindrical shape and of low height, of "token" or "pallet" type. Such a shape is perfectly suitable for subsequent machining of these polymer blocks in order to obtain intraocular lenses.

Obviously, direct molding of the intraocular lenses is also possible with a suitable mold.

The polymer blocks are then purified in order to remove monomers not having reacted and residual products notably arising from the synthesis of each of the monomers used.

The blocks of polymer material are then ready to be machined at a temperature lower than the polymer's vitreous transition temperature, in order to produce intraocular lenses according to the invention.

In order to perfectly describe the invention, two examples of the acrylic polymer material according to the invention are explained in detail below.

EXAMPLE 1

The acrylic polymer material has been obtained by radical polymerization from the following initial mixture: (The quantities are expressed as weight percentages of the initial mixture before polymerization.)

Monomers:

| | |
|---|---|
| 2 phenoxy-ethylacrylate | 76.1% |
| 2-phenoxy-tetraethylene glycol acrylate | 6% |
| 4-hydroxy-butyl acrylate | 9.7% |
| hydroxy-ethyl methacrylate | 4% |
| tetraethylene glycol diacrylate | 0.6% |
| tetraethylene glycol dimethacrylate | 2% |
| anti-UV agent | 0.5% |

Initiator Compound:

| | |
|---|---|
| lauroyl diperoxide | 0.5% |
| tert-amyl-peroxy-2-ethyl-hexyl-carbonate | 0.5% |

Transfer Agent:

| | |
|---|---|
| thiol octane | 0.1% |

After polymerization at 90° C. for a period of 10 hours, one thus obtains an acrylic polymer material with an optical index of 1.545 and a vitreous transition temperature substantially equal to 10° C.

EXAMPLE 2

The acrylic polymer material has been obtained by radical polymerization from the following initial mixture: (The quantities are expressed as weight percentages of the initial mixture before polymerization.)
Monomers:

| | |
|---|---|
| 2 phenoxy-ethylacrylate | 77% |
| 2-phenoxy-tetraethylene glycol acrylate | 8% |
| 4-hydroxy-butyl acrylate | 8% |
| hydroxy-ethyl methacrylate | 3% |
| tetraethylene glycol diacrylate | 0.4% |
| tetraethylene glycol dimethacrylate | 1.5% |
| triethylene glycol dimethacrylate | 0.5% |
| anti-UV agent | 0.5% |

Initiator Compound:

| | |
|---|---|
| lauroyl diperoxide | 1% |

Transfer Agent:

| | |
|---|---|
| thiol octane | 0.1% |

After polymerization at 90° C. for a period of 10 hours, one thus obtains an acrylic polymer material with an optical index of 1.545 and a vitreous transition temperature substantially equal to 9° C.

To highlight the surprising advantages of the material according to the invention in relation to prior art, and to demonstrate its low susceptibility to glistening and its characteristic of low adherence to itself, a series of tests has been performed in order to compare the properties of the material according to the invention, with regard to the material described in the prior patent application FR 2 930 731.

Several polymer materials were produced from the same arylalkoxy-acrylate (2-phenoxy-ethylacrylate), hydroxylated acrylate (4-hydroxy-butyl acrylate), hydroxylated methacrylate (hydroxy-ethyl methacrylate), diol diacrylate (tetraethylene glycol diacrylate) and diol dimethacrylate (tetraethylene glycol dimethacrylate).

Certain of them were produced in accordance with the formula of prior patent application FR 2 930 731, with the addition of an alkylacrylate, namely the butyl acrylate called ABU.

The others were produced in accordance with the formula of the present invention, with the addition of the same quantities of the following instead: 2-phenoxy-(2-ethoxy)n-acrylate, with 4≤n≤6, namely the 2-phenoxy-2-ethoxy-2-ethoxy-2-ethoxy-acrylate called 4PEA.

The same quantity of transfer agent (thiol octane) was added in all cases.

To obtain different polymer materials to test, the percentage of hydroxylated monomers (hydroxylated acrylate and methacrylate) and of butyl acrylate (ABU) for the polymers according to prior art was varied; the same applies for the percentage of hydroxylated monomers (hydroxylated acrylate and methacrylate) and of 4PEA for the polymers according to the invention; the same quantities of the other monomers were used.

The obtained polymer materials were then subjected to two series of tests: a glistening measurement test and a test of self-adherence in water.

Glistening Measurement Test:

Intraocular lenses were manufactured with the different polymer materials obtained and they were immersed in water at 35° C. for one month.

They then underwent a test to measure the glistening index that was developed by L. Werner and which consists in observing each lens under a microscope, taking a photograph with a slot lamp, counting the number of glistening points visible in the photograph, and comparing it with a reference scale in order to assign the lens an index between 0 and 5.

The results obtained with the different materials tested are stated in the table below:

| Polymer of prior art (according to FR 2 930 731) | | | Polymer according to the invention | | |
|---|---|---|---|---|---|
| Percentage of hydroxylated monomers (acrylate + methacrylate) | Percentage of ABU | Glistening index | Percentage of hydroxylated monomers (acrylate + methacrylate) | Percentage of 4PEA | Glistening index |
| 13 | 6 | 2 | 13 | 6 | 0.5 |
| 10 | 6 | 3 | 10 | 6 | 0.5 |
| 15 | 4 | 2 | 15 | 4 | 1.5 |
| 13 | 10 | 5 | 13 | 10 | 0.5 |
| 15 | 8 | 4 | 15 | 8 | 2 |

One observes that with an identical percentage of hydroxylated monomers and a percentage of 4PEA comparable to that of the butyl acrylate (ABU), the polymer materials according to the invention have a glistening index that is considerably lower than that of equivalent prior polymer materials.

Test of Self-Adhesion in Water:

Using the polymer materials obtained, strips 5 cm long, 3 cm wide and 3 mm thick were produced.

These strips were placed in water at 25° C. They were then folded in their central area and folded back on themselves so as to ensure adhesion of the interior surfaces, which were in contact. After having maintained a pressure by pressing in parallel at the fold for one minute, the folded strips were relieved of any stress.

The time necessary for the strips to deploy themselves completely and return to a horizontal arrangement was then measured. The time, measured in seconds, is characteristic of the tackiness of the material, namely its characteristic of self-adherence.

The results obtained with the different materials tested are stated in the table below:

| Polymer of prior art (according to FR 2 930 731) | | | Polymer according to the invention | | |
|---|---|---|---|---|---|
| Percentage of hydroxylated monomers (acrylate + methacrylate) | Percentage of ABU | Adhesion time (seconds) | Percentage of hydroxylated monomers (acrylate + methacrylate) | Percentage of 4PEA | Adhesion time (seconds) |
| 13 | 6 | 30 | 13 | 6 | 10 |
| 10 | 6 | 30 | 10 | 6 | 15 |
| 15 | 4 | 35 | 15 | 4 | 10 |
| 13 | 10 | >60 | 13 | 10 | 20 |
| 15 | 8 | 20 | 15 | 8 | 5 |

One observes that with an identical percentage of hydroxylated monomers and a percentage of 4PEA comparable to that of the butyl acrylate (ABU), the polymer materials according to the invention deploy in much less time than the equivalent prior polymer materials. Therefore, they have much less tendency to self-adhere than prior polymer materials, which is a considerable advantage when implanting the intraocular lenses.

Obviously, the invention is not limited to the preferential embodiments described above and illustrated in the various Figures; a man skilled in the art can make many modifications and imagine other variants without going beyond the range or scope of the invention.

The invention claimed is:

1. A hydrophobic acrylic polymer material, wherein said material is a cross-linked co-polymer of at least the following monomers:
   an arylalkoxy-acrylate different from a 2-phenoxy-(2-ethoxy)$_n$-acrylate with $4 \leq n \leq 6$;
   a 2-phenoxy-(2-ethoxy)$_n$-acrylate with $4 \leq n \leq 6$;
   a hydroxylated acrylate;
   a hydroxylated methacrylate;
   an ethoxylated diol diacrylate; and
   an ethoxylated diol dimethacrylate;
and wherein said cross-linked copolymer takes the form of a three-dimensional macromolecular network with hanging chains, due to the presence of at least one transfer agent in the monomer mixture during the cross-linking.

2. The hydrophobic acrylic polymer material according to claim 1, wherein the arylalkoxy-acrylate different from a 2-phenoxy-(2-ethoxy)$_n$-acrylate with $4 \leq n \leq 6$ is a compound chosen from 2-phenoxy-ethylacrylate, 2-phenoxy-2-ethoxy-ethylacrylate and 2-phenoxy-2-ethoxy-2-ethoxy-ethylacrylate.

3. The hydrophobic acrylic polymer material according to claim 1, wherein the 2-phenoxy-(2-ethoxy)$_n$-acrylate with $4 \leq n \leq 6$ is 2-phenoxy-2-ethoxy-2-ethoxy-2-ethoxy-2-ethoxy-acrylate.

4. The hydrophobic acrylic polymer material according to claim 1, wherein the hydroxylated acrylate is a dihydroxy-alkyl monoacrylate or a dihydroxy-ethoxy-alkyl monoacrylate of which the alkyl chain of the glycol incorporates 3 to 6 carbon atoms, and wherein the hydroxylated methacrylate is a dihydroxy-alkyl monomethacrylate or a dihydroxy-ethoxy-alkyl monomethacrylate of which the alkyl chain of the glycol incorporates 3 to 6 carbon atoms.

5. The hydrophobic acrylic polymer material according to claim 1, wherein the ethoxylated diol diacrylate is triethylene glycol diacrylate or tetraethylene glycol diacrylate; and wherein the ethoxylated diol dimethacrylate is triethylene glycol dimethacrylate or tetraethylene glycol dimethacrylate.

6. The hydrophobic acrylic polymer material according to claim 1, wherein it is a cross-linked co-polymer of at least the following monomers:
   2-phenoxy-ethylacrylate;
   2-phenoxy-2-ethoxy-2-ethoxy-2-ethoxy-2-ethoxy-acrylate;
   4-hydroxy-butyl acrylate;
   hydroxy-ethyl methacrylate;
   tetraethylene glycol diacrylate;
   tetraethylene glycol dimethacrylate.

7. The hydrophobic acrylic polymer material according to claim 1, wherein it is a cross-linked co-polymer of at least the monomers according to claim 1, in the following weight proportions:
   between 45 and 84% of arylalkoxy-acrylate different from a 2-phenoxy-(2-ethoxy)$_n$-acrylate with $4 \leq n \leq 6$;
   between 3 and 15% of 2-phenoxy-(2-ethoxy)$_n$-acrylate with $4 \leq n \leq 6$;
   between 11 and 15% of hydroxylated acrylate and hydroxylated methacrylate;
   between 1 and 3% of ethoxylated diol diacrylate and ethoxylated diol dimethacrylate.

8. The hydrophobic acrylic polymer material according to claim 7, wherein the relative proportion between the hydroxylated acrylate and the hydroxylated methacrylate and between the ethoxylated diol diacrylate and the ethoxylated diol dimethacrylate varies for each pair from 20 to 80% of one relative to the other.

9. The hydrophobic acrylic polymer material according to claim 7, wherein the 2-phenoxy-(2-ethoxy)$_n$-acrylate is 2-phenoxy-2-ethoxy-2-ethoxy-2-ethoxy-2-ethoxy-acrylate, and in that the weight proportion of 2-phenoxy-2-ethoxy-2-ethoxy-2-ethoxy-2-ethoxy-acrylate is comprised between 4 and 10%.

10. The hydrophobic acrylic polymer material according to claim 1, wherein it is a cross-linked co-polymer of at least the monomers according to claim 1 and of a UV-absorbing monomer.

11. A method for the production of a hydrophobic acrylic polymer material according to claim 1, that the method comprising:
   radically polymerizing, in one single polymerization step, a mixture containing at least:
      an arylalkoxy-acrylate different from a 2-phenoxy-(2-ethoxy)$_n$-acrylate with $4 \leq n \leq 6$;
      a 2-phenoxy-(2-ethoxy)$_n$-acrylate with $4 \leq n \leq 6$;
      a hydroxylated acrylate;
      a hydroxylated methacrylate;
      an ethoxylated diol diacrylate;
      an ethoxylated diol dimethacrylate; and
      a transfer agent;
   thereby obtaining, by said polymerizing, a three-dimensional macromolecular network with hanging chains.

12. The method according to claim 11, wherein the mixture also includes at least one initiator compound.

13. The method according to claim 12, wherein said at least one initiator compound is chosen from alkyl peroxides, lauroyl diperoxide, 1,1-di-ter-butylperoxycyclohexane, and tert-amyl-peroxy-2-ethyl-hexyl-carbonate.

14. The method according to claim 11, wherein the transfer agent is thiol butane or thiol octane.

15. The method according to claim 11, wherein the mixture comprises between 0.03 and 0.2% by weight of transfer agent.

16. An intraocular lens comprising the hydrophobic acrylic polymer material according to claim 1.

17. The hydrophobic acrylic polymer material according to claim 2, wherein the 2-phenoxy-(2-ethoxy)$_n$-acrylate with $4 \leq n \leq 6$ is 2-phenoxy-2-ethoxy-2-ethoxy-2-ethoxy-2-ethoxy-acrylate.

18. The hydrophobic acrylic polymer material according to claim 2, wherein the hydroxylated acrylate is a dihydroxy-alkyl monoacrylate or a dihydroxy-ethoxy-alkyl monoacrylate of which the alkyl chain of the glycol incorporates 3 to 6 carbon atoms, and wherein the hydroxylated methacrylate is a dihydroxy-alkyl monomethacrylate or a dihydroxy-ethoxy-alkyl monomethacrylate of which the alkyl chain of the glycol incorporates 3 to 6 carbon atoms.

19. The hydrophobic acrylic polymer material according to claim 3, wherein the hydroxylated acrylate is a dihydroxy-alkyl monoacrylate or a dihydroxy-ethoxy-alkyl monoacrylate of which the alkyl chain of the glycol incorporates 3 to 6 carbon atoms, and wherein the hydroxylated methacrylate is a dihydroxy-alkyl monomethacrylate or a dihydroxy-ethoxy-alkyl monomethacrylate of which the alkyl chain of the glycol incorporates 3 to 6 carbon atoms.

20. The hydrophobic acrylic polymer material according to claim 6, comprising:
  between 45 and 84% of 2-phenoxy-ethylacrylate;
  between 3 and 15% of 2-phenoxy-2-ethoxy-2-ethoxy-2-ethoxy-2-ethoxy-acrylate;
  between 11 and 15% of total 4-hydroxy-butyl acrylate and hydroxy-ethyl methacrylate;
  between 1 and 3% of total tetraethylene glycol diacrylate and tetraethylene glycol dimethacrylate.

* * * * *